US006932824B1

(12) United States Patent
Roop et al.

(10) Patent No.: US 6,932,824 B1
(45) Date of Patent: Aug. 23, 2005

(54) THREE-NEEDLE CLOSURE DEVICE

(75) Inventors: John Avi Roop, Crystal, MN (US); Kedar R. Belhe, Minnetonka, MN (US); Catherine A. Pipenhagen, Chanhassen, MN (US)

(73) Assignee: St. Jude Medical Puerto Rico B.V., Amsterdam (NL)

( * ) Notice: Subject to any disclaimer, the term of this patent is extended or adjusted under 35 U.S.C. 154(b) by 9 days.

(21) Appl. No.: 10/791,097

(22) Filed: Mar. 2, 2004

(51) Int. Cl.[7] ............................................. A61B 17/04
(52) U.S. Cl. ...................... 606/139; 606/144; 606/148
(58) Field of Search .................... 606/113, 145, 144, 606/148; 289/17; 600/104; 604/105–108

(56) References Cited

U.S. PATENT DOCUMENTS

| 4,602,635 | A |   | 7/1986  | Mulhollan et al. ........... 128/334 |
|-----------|---|---|---------|-------------------------------------|
| 5,025,778 | A | * | 6/1991  | Silverstein et al. .......... 600/104 |
| 5,217,001 | A | * | 6/1993  | Nakao et al. ................ 600/123 |
| 5,304,184 | A |   | 4/1994  | Hathaway et al. ........... 606/144 |
| 5,376,096 | A |   | 12/1994 | Foster ......................... 606/147 |
| 5,403,329 | A |   | 4/1995  | Hinchcliffe ................. 606/147 |
| 5,417,699 | A |   | 5/1995  | Klein et al. .................. 606/144 |
| 5,423,830 | A | * | 6/1995  | Schneebaum et al. ...... 606/115 |
| 5,462,561 | A |   | 10/1995 | Voda ............................ 606/144 |
| 5,476,469 | A |   | 12/1995 | Hathaway et al. ........... 606/144 |
| 5,507,757 | A | * | 4/1996  | Sauer et al. ................. 606/144 |
| 5,607,435 | A | * | 3/1997  | Sachdeva et al. ............ 606/139 |
| 5,613,974 | A |   | 3/1997  | Andreas et al. .............. 606/144 |
| 5,626,588 | A |   | 5/1997  | Sauer et al. ................. 606/144 |
| 5,662,681 | A |   | 9/1997  | Nash et al. .................. 606/213 |
| 5,720,757 | A |   | 2/1998  | Hathaway et al. ........... 606/144 |
| 5,755,727 | A |   | 5/1998  | Kontos ........................ 606/144 |
| 5,782,861 | A |   | 7/1998  | Cragg et al. ................. 606/216 |
| 5,814,065 | A |   | 9/1998  | Diaz ............................ 606/213 |
| 5,817,013 | A | * | 10/1998 | Ginn et al. .................. 600/114 |
| 5,919,207 | A |   | 7/1999  | Taheri ......................... 606/219 |
| 5,980,539 | A |   | 11/1999 | Kontos ........................ 606/148 |
| 5,984,932 | A | * | 11/1999 | Yoon ........................... 606/147 |
| 6,117,144 | A |   | 9/2000  | Nobles et al. ............... 606/144 |
| 6,352,503 | B1 | * | 3/2002 | Matsui et al. ................ 600/104 |
| 6,761,685 | B2 | * | 7/2004 | Adams et al. ............... 600/121 |
| 2004/0059352 | A1 | * | 3/2004 | Burbank et al. ............. 606/148 |

OTHER PUBLICATIONS

Merriam-Webster OnLine Dictionary: definition of "expand": one page. printed Mar. 9, 2005.*

* cited by examiner

Primary Examiner—Anhtuan T. Nguyen
Assistant Examiner—Bradford C Pantuck
(74) Attorney, Agent, or Firm—Holland & Hart

(57) ABSTRACT

The present invention relates to a three-needle type vascular closure system. The closure system utilizes three needles in the form of a guiding device, an expandable needle, and a hooking device. The guiding device is used to make the initial opening in the vessel, where the opening provides access for a sheath through which a medical procedure is to be performed. The expandable needle is inserted into the vessel in which it expands radially from the needle to form a target. The hooking device is also inserted into the vessel and is used to hook the expandable needle so as to form an internal union between the hooking device and the expandable needle. The needles can then be retracted thereby extending a suture from the hooking device and forming an internal suture pass that can be used to approximate the tissue surrounding the initial opening in the vessel. In one embodiment, the suture is passed across the vessel opening prior to dilation of the vessel opening.

12 Claims, 10 Drawing Sheets

THREE-NEEDLE CLOSURE DEVICE

FIELD OF THE INVENTION

This invention relates to suturing devices. More specifically, this invention relates to suturing devices for approximating tissue surrounding an opening in a corporeal vessel wall.

BACKGROUND OF THE INVENTION

Various medical procedures, particularly cardiology procedures, involve accessing a corporeal vessel through a percutaneous sheath. The sheath necessarily requires the formation of a hole or opening in the vessel wall so that a medical procedure can be performed via the sheath. After the particular medical procedure has been performed, the sheath must eventually be removed from the vessel and the access hole in the vessel wall must be closed.

A number of prior vascular closure devices and methods have been developed in attempting to provide a solution for the problem of closing a hole in the vessel wall. Tissue approximation typically involves passing a length of suture into and through adjacent vessel and subcutaneous tissue, across the vessel opening, and back into and through adjacent vessel and subcutaneous tissue. Certain prior closure devices have involved relatively complicated methods and devices for extracting a length of suture from inside the vessel so that the physician can approximate tissue surrounding the hole in the vessel wall through use of the suture.

U.S. Pat. No. 5,643,292 and U.S. Pat. No. 6,059,800 disclose example prior suturing devices used for approximating tissue surrounding the opening in a vessel wall. Most prior closure devices enlarge the vessel opening thereby negating the benefits of using smaller or less invasive percutaneous products. Prior suturing devices are also relatively complicated and difficult to use. Furthermore, many suturing devices dilate the vessel opening and perform the medical procedure via the vessel opening before the suture is extended across the vessel opening for approximation tissue surrounding the vessel wall.

There remains a need, therefore, to provide a suture apparatus that is relatively simple in construction, is easy to use, and can effectively approximate tissue surrounding an opening in a vessel wall. There is further a need to provide a suturing device that minimizes the invasiveness of the suturing procedure.

SUMMARY OF THE INVENTION

The present invention relates to a three-needle type preclosure vascular suture device. The pre-closure system utilizes three needles in the form of a guiding device, an expandable needle, and a hooking device. The guiding device is used to align the vascular closure system with a vessel in which a vessel opening is to be first dilated and subsequently closed. The expandable needle is inserted into the vessel in which it expands radially from the needle to form a target. The hooking device is also inserted into the vessel and is used to hook the expandable needle so as to form an internal union between the hooking device and the expandable needle. The needles can then be retracted thereby extending a suture from the hooking device and forming an internal suture pass that can eventually be used to approximate the tissue surrounding the opening in the vessel. After the suture pass has been put in place across the opening, the vessel opening is then dilated by a sheath, or by some other suitable method, and a medical procedure would be performed through such a sheath. After the medical procedure, the already-in-place suture can be used to approximate tissue.

The foregoing and other features, utilities, and advantages of the invention will be apparent from the following detailed description of the invention with reference to the accompanying drawings.

DETAILED DESCRIPTION OF THE INVENTION

The present invention relates to a three-needle type closure system. The closure system comprises a "pre-closure" system because it extends a suture across a vessel opening before the opening is dilated so that a medical procedure can be performed. The system utilizes three needles in the form of a guiding device, an expandable needle, and a hooking device. The guiding device is used to align the vascular closure system with a vessel in which an opening is to be dilated. The expandable needle is inserted into the vessel in which it expands radially from the needle to form a target. The hooking device is also inserted into the vessel and is used to hook the expandable needle so as to form an internal union between the hooking device and the expandable needle. The needles can then be retracted thereby extending a suture from the hooking device and forming an internal suture pass that can be used to approximate the tissue surrounding the vessel opening after a medical procedure has been performed. Also, while embodiments of the present invention are directed toward a vascular closure system for use in connection with a medical procedure, the teachings of the present invention are applicable in other areas as well.

Figure 1:
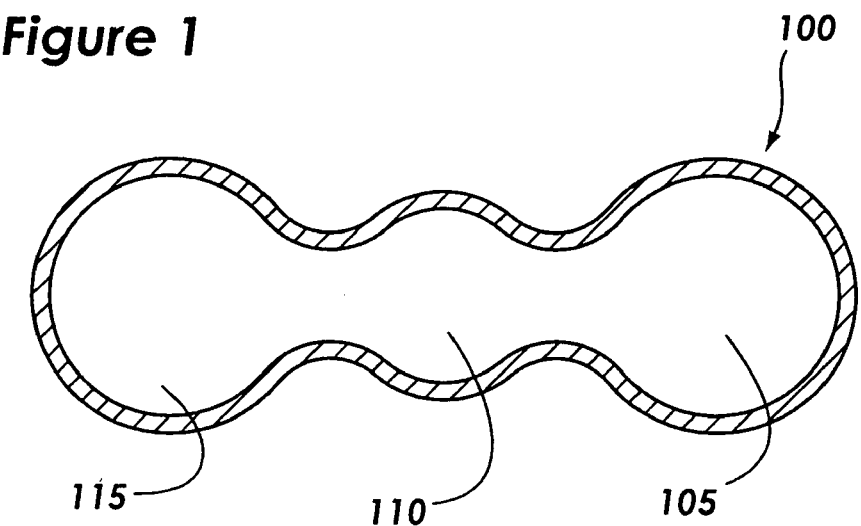
FIG. 1 is a frontal view of a vascular closure system including a hollow sheath forming three lobes in accordance with one embodiment of the present invention.

FIG. 1 illustrates a front view of the hollow sheath in accordance with one embodiment of the present invention. The hollow sheath 100 includes three lobes: a left lobe 115, a center lobe 110, and a right lobe 105. The lobes 105, 110, 115 are substantially cylindrical enclosures. The sheath 100 comprises stainless steel and is formed by a stamping process. The stamping process allows an 8 French circumference to be preserved to ensure that there is no dilation of the tissue tract (i.e., the tissue above the artery). The edges of the sheath are smoothed to minimize friction when extending and retracting needles from the three lobes 105, 110, 115.

Figure 2:
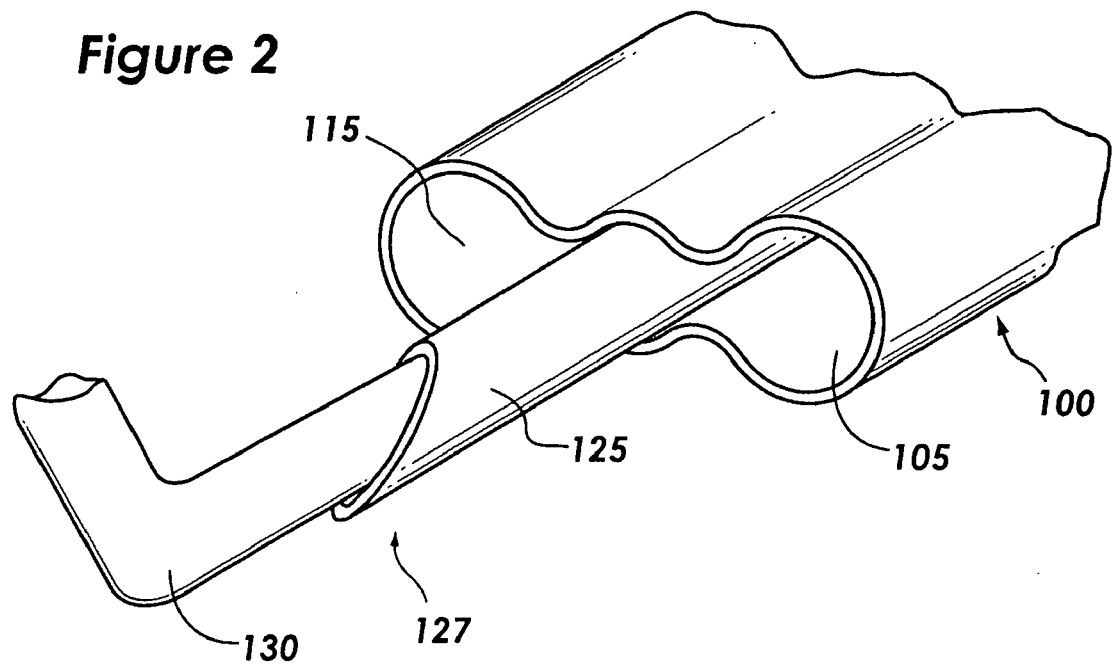
FIG. 2 is a perspective view of the vascular closure system of FIG. 1 with an access needle and guide wire being extended from the center lobe of the sheath.

A guiding device 127 is disposed within the center lobe 110 of the sheath 100 as shown in FIG. 2. The guiding device 127 includes a guide wire 130 and an access needle 125. The guide wire 130 is contained within the access needle 125 so as to allow the access needle 125 to initially pierce the vessel and then be extended within. The guiding device 127 is inserted into an unpierced vessel, or alternatively in an existing hole in the vessel in order to gain access to the interior of the vessel. The guide wire 130 may comprise nitinol and initially includes a 90-degree bend. The access needle 125 comprises stainless steel and is shaped in a grinding process to form a standard cutting needle point. Once the guiding device 127 is inserted within the vessel, the guide wire 130 is further extended so as to conform to the interior shape of the vessel thereby providing a user of the vascular closure system tactile feedback of the vessels dimensions. The operation of the guiding device 127 in relation to the entire vascular closure system is described in more detail with reference to FIG. 5 and the vascular closure process described with reference to FIGS. 8–16.

Figure 3:
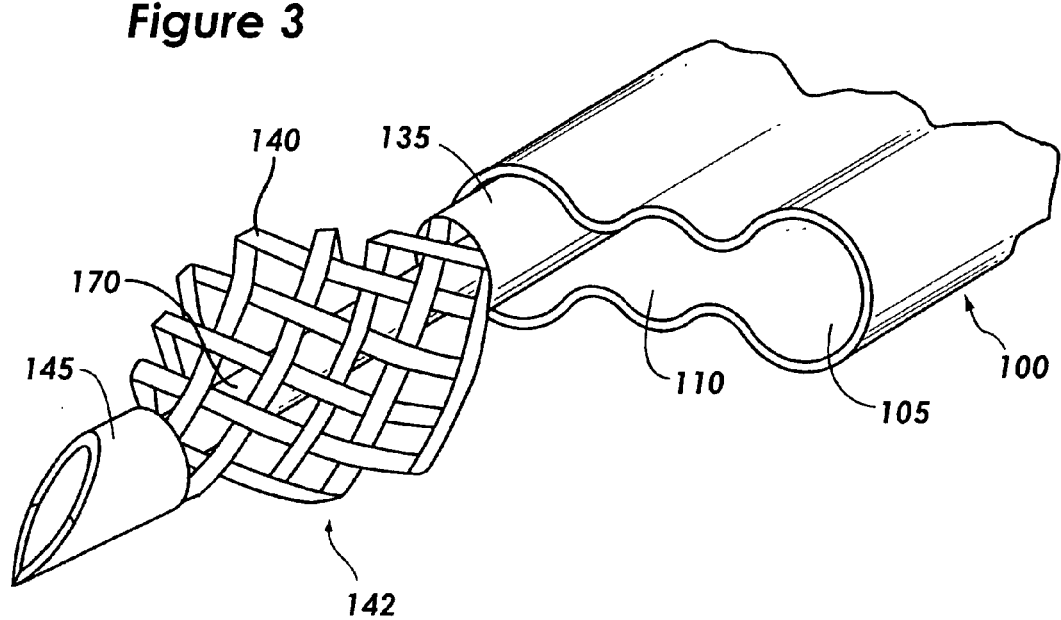
FIG. 3 is a perspective view of the vascular closure system of FIG. 1 with an expandable needle extended from the left lobe of the sheath.

An expandable needle 142 is disposed within the left lobe 115 of the sheath as shown in FIG. 3. The expandable needle 142 further includes an actuator 135, an expandable mesh 140, an insertion rod 170, and a needle tip 145. The actuator 135 is an actuation mandrel that is used to compress and expand the expandable mesh 140 once it is inside the vessel. The expandable mesh 140 is a tubular braid that can be extended or expanded. The expandable mesh 140 is disposed over the insertion rod 170. The insertion rod 170 is used to insert the entire expandable needle 142 without expanding the expandable mesh 140. The needle tip 145 comprises stainless steel and is shaped in a grinding process to conform to a standard cutting needle point. The needle tip 145 is used to pierce the vessel during the insertion of the expandable needle 142. The operation of the expandable needle 142 in relation to the entire vascular closure system is described in more detail with reference to FIGS. 6A and 6B and the vascular closure process described with reference to FIGS. 8–16.

Figure 4:
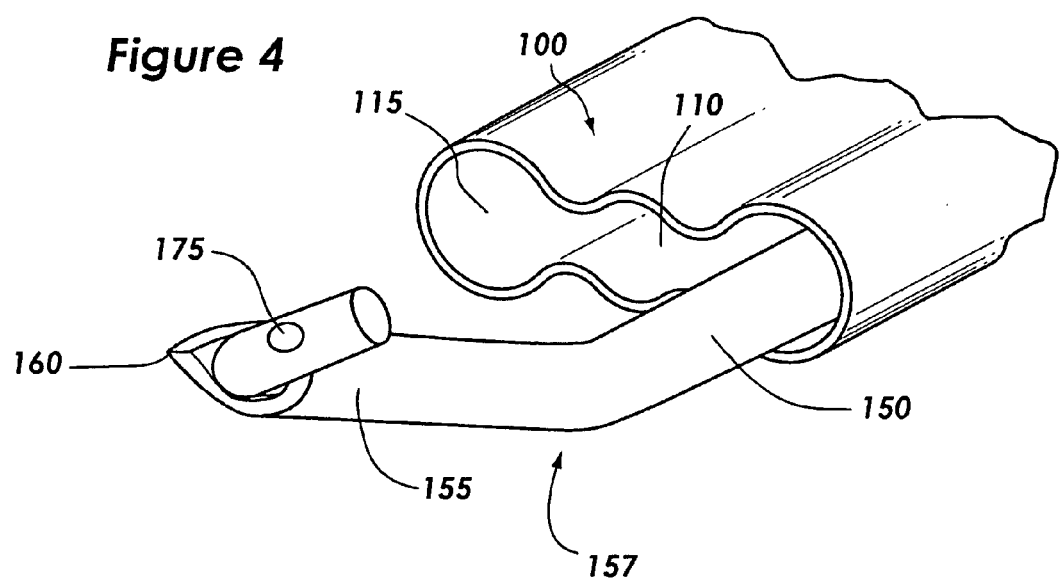
FIG. 4 is a perspective view of the vascular closure system of FIG. 1 with a curved needle and piercing toggle extended from a right lobe of the sheath.

A hooking device 157 is disposed within the right lobe 105 of the sheath 100 as shown in FIG. 4. The hooking device 157 further includes a curved hollow needle 150, a suture 175 (FIGS. 14 and 15), and a piercing toggle 155. The curved hollow needle 150 is a tubular, super-elastic needle shaped in a grinding process to conform to a standard cutting needle point. The curved hollow needle 150 is curved in a manner to coincide with the expanded mesh. The curved hollow needle 150 further includes a needle tip 160, which is sharpened to facilitate the actual piercing of the vessel. The suture 175 is a standard medical suture that extends throughout the curved hollow needle 150 and is attached to the piercing toggle 155. The suture 175 comprises a degradable material that will eventually degrade within a human body. The piercing toggle 155 comprises a stainless steel wire portion that is specifically beveled to facilitate hooking and piercing. The piercing toggle 155 is disposed near the tip 160 of the curved needle 150 and is attached to the suture 175 (FIGS. 14 and 15). The piercing toggle 155 includes a hole at its proximal end to facilitate attachment with the suture 175. The operation of the hooking device 157 in relation to the entire vascular closure system is described in more detail with reference to FIGS. 7A and 7B and the vascular closure process described with reference to FIGS. 8–16.

Figure 5:
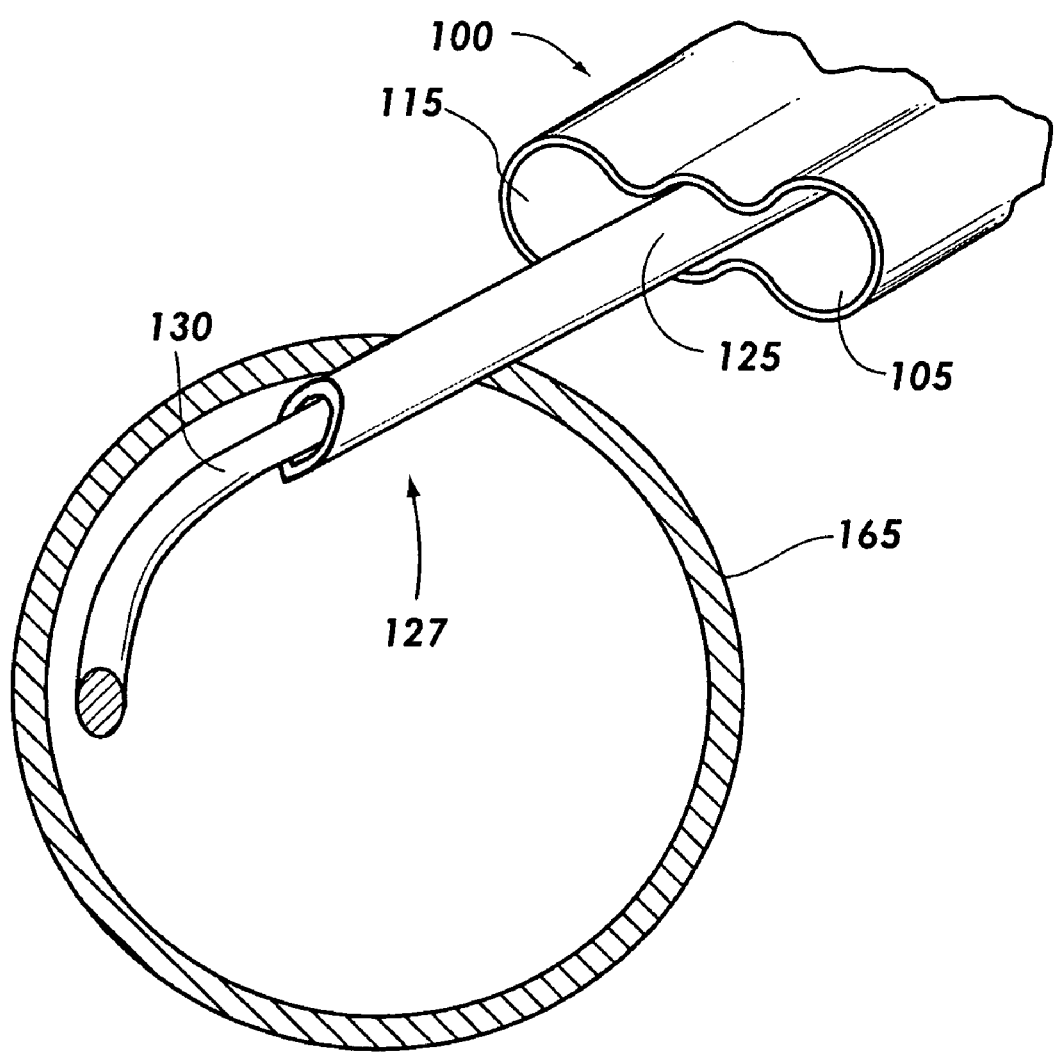
FIG. 5 is a perspective view of the vascular closure system of FIG. 1 with a guide wire extended from the center lobe of the sheath to within a portion of the interior wall of a vessel.

FIG. 5 illustrates the positioning of the guiding device 127 in relation to the vessel when the guide wire 130 is extended into the vessel 165. As discussed above, the guide wire 130 comprises a material that is able to bend and conform to the shape of the interior surface of the vessel. The tactile feedback received from the guiding device 127 allows the sheath 100 to be properly positioned over the vessel 165 as shown. Alternatively, other methods may be used to properly position the sheath 100 and remain consistent with this invention. For example, a set of feet could be extended from the guiding device 127 and then retracted against the interior surface of the vessel 165 to provide a similar tactile feedback as to the position of the sheath 100 in relation to the vessel 165.

Figure 6A:
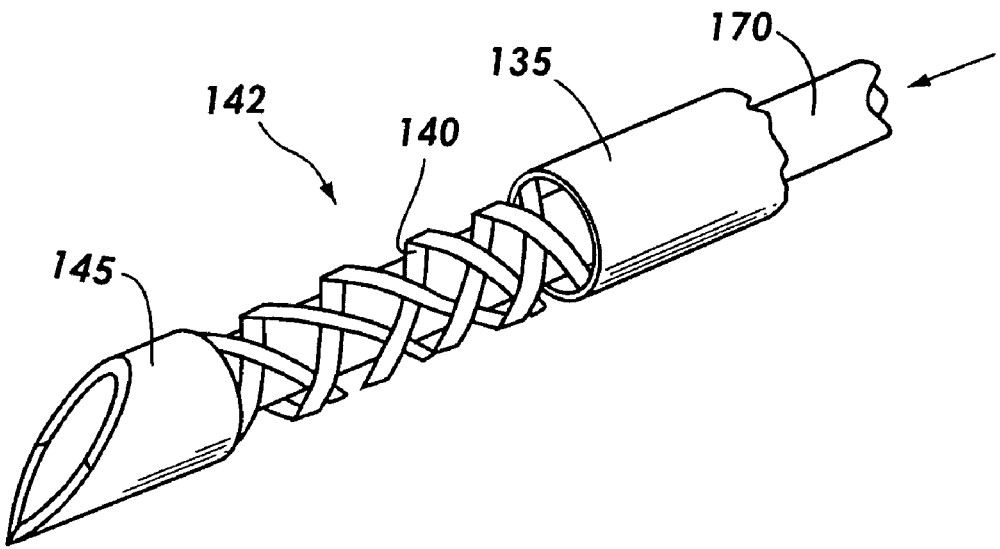
FIG. 6A is a perspective view of the expandable needle illustrated in FIG. 3 showing the expandable needle in an extended state.
Figure 6B:
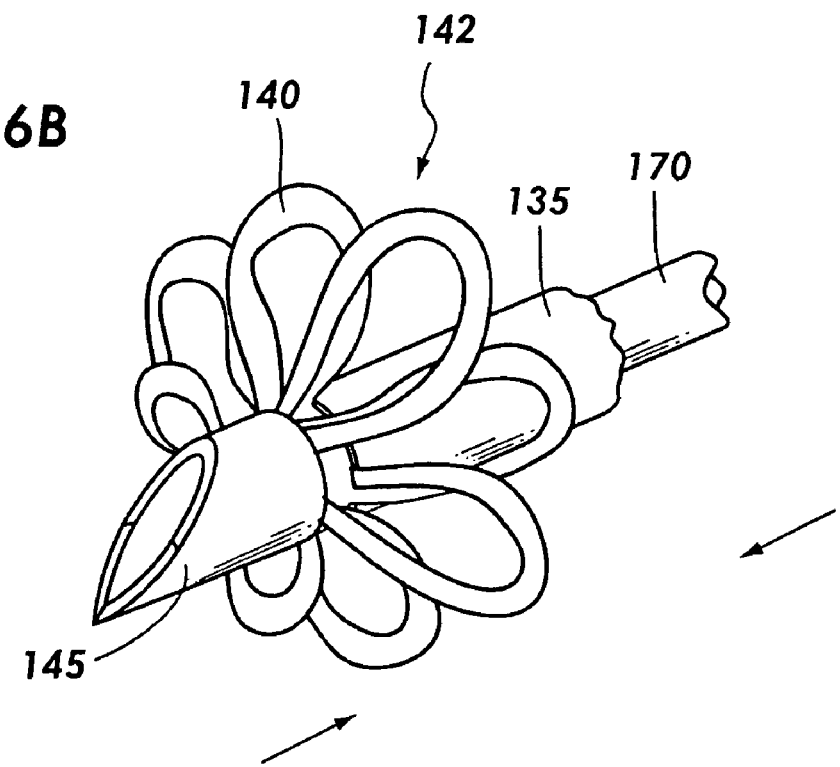
FIG. 6B is a perspective view of the expandable needle illustrated in FIG. 3 showing the expandable needle in a expanded state.

FIGS. 6A and 6B illustrate the operation of the expandable needle 142 showing an extended state and an expanded state respectively. The expandable needle 142 is initially inserted into a vessel in the extended state shown in FIG. 6A. The expandable mesh 140 is kept from expanding during insertion by applying the necessary insertion force on the insertion rod 170 rather than the actuator 135 thereby preventing a compression force from being exerted on the expandable mesh 140. Once the expandable needle 142 is inserted into a vessel, the actuator 135 is extended distally thereby exerting a compression force on the expandable mesh 140 between the actuator 135 and the needle tip 145. When a compression force is exerted onto the expandable mesh 140, the expandable mesh 140 expands into the expanded state shown in FIG. 6B. The expanded state laterally extends mesh loops radially away from the center of the expandable needle 142 thereby providing a clear target for the hooking device 157.

Figure 7A:
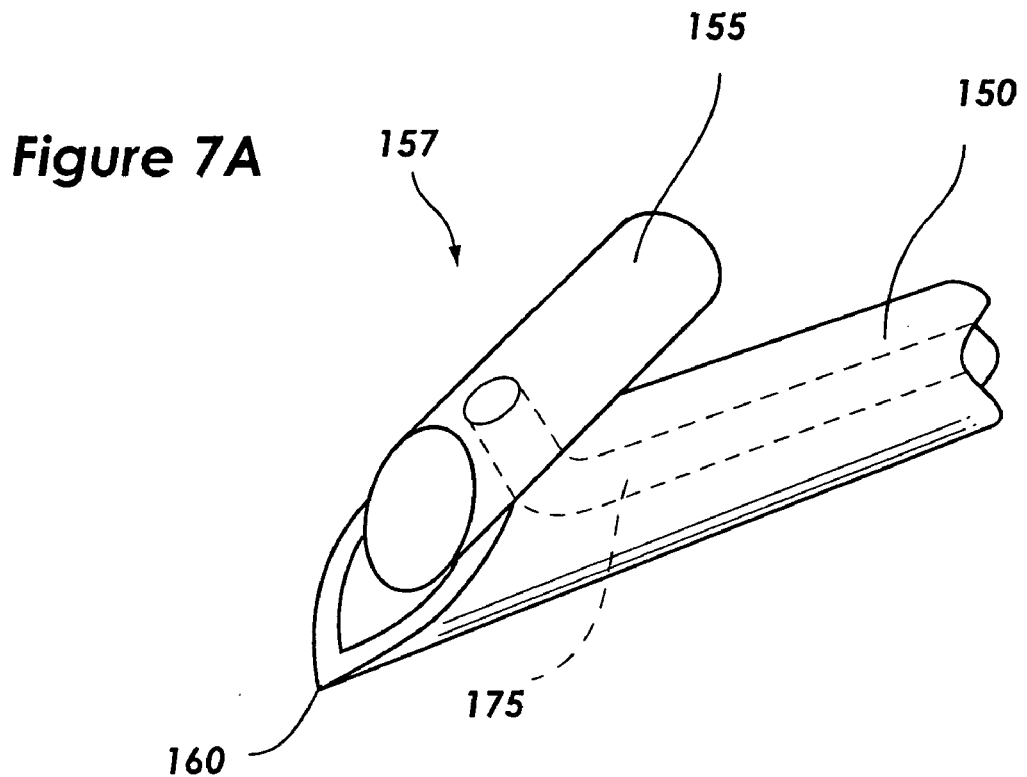
FIG. 7A is a perspective view of the curved needle and piercing toggle illustrated in FIG. 4 showing the suture in phantom.
Figure 7B:
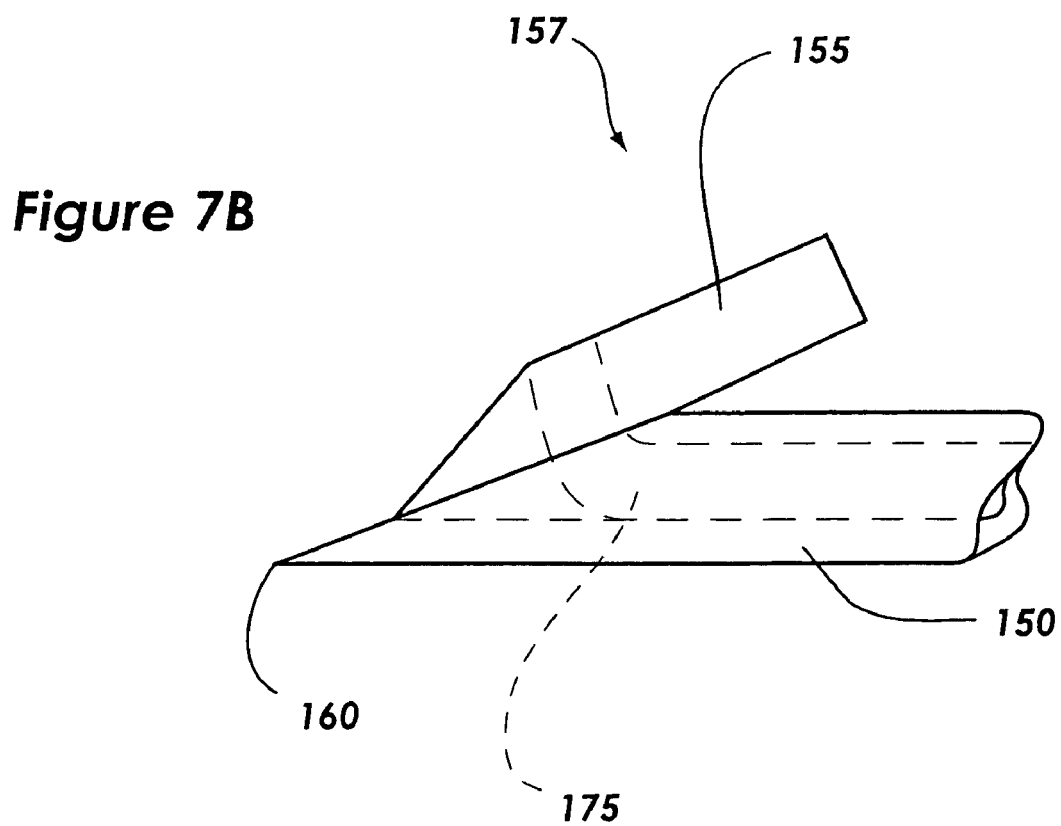
FIG. 7B is a profile view of the curved needle and piercing toggle illustrated in FIG. 4 showing the suture in phantom.

FIGS. 7A and 7B illustrate the shape of the hooking device 157. The hooking device 157 is generally inserted into a vessel after the guiding device 127 and the expandable needle 142. FIGS. 7A and 7B illustrate a perspective view and a profile view of the hooking device 157 respectively. The perspective view illustrated in FIG. 7A shows the approximate position of the piercing toggle 155 in relation to the curved needle 150. In addition, the suture 175 has been illustrated in phantom to show how it extends internally through the curved needle 150. The piercing toggle 155 angles up and over the top of the curved needle to form a hooking section that is used to hook the expandable mesh 140 of the expandable needle 142. The profile view shown in FIG. 7B also shows the position of the piercing toggle 155 in relation to the tip 160 of the curved needle 150. The upper portion of the tip 160 of the curved needle 150 and the piercing toggle 155 forms a continuous piercing surface. The gap between the piercing toggle 155 and the curved needle 150 form the hooking section that is used to hook the expandable mesh 140 of the expandable needle 142.

Figure 8:
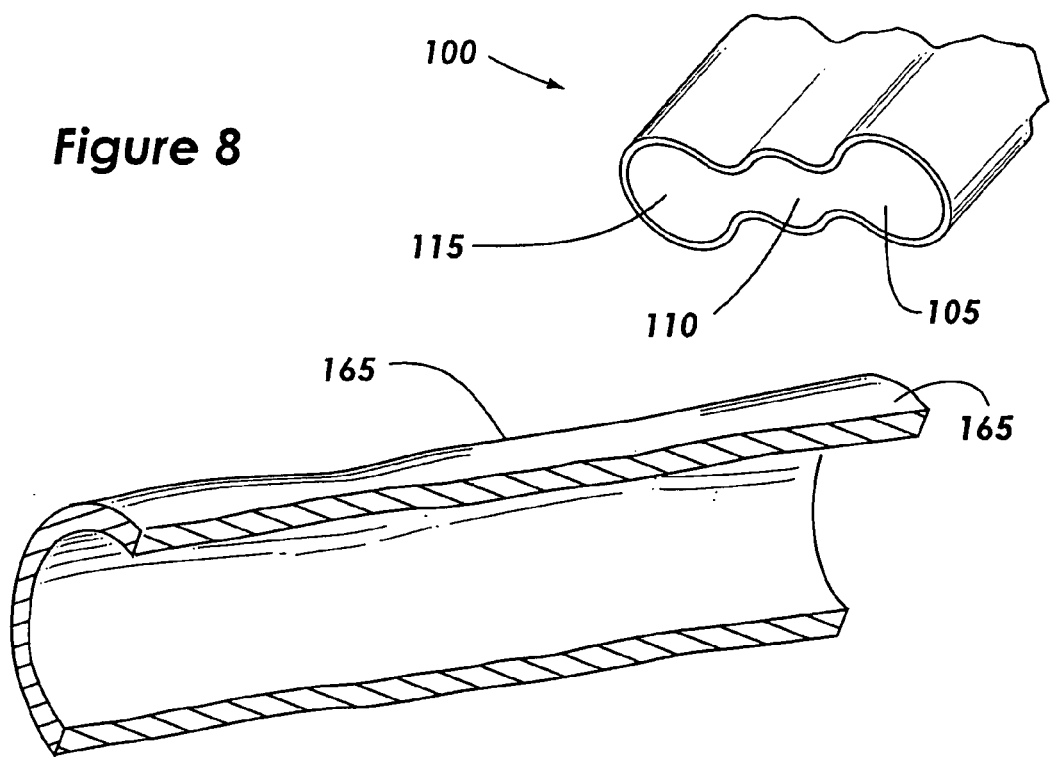
FIG. 8 is a perspective view of the vascular closure system of FIG. 1 being properly positioned over a vessel in preparation for pre-closing a vascular opening.
Figure 9:
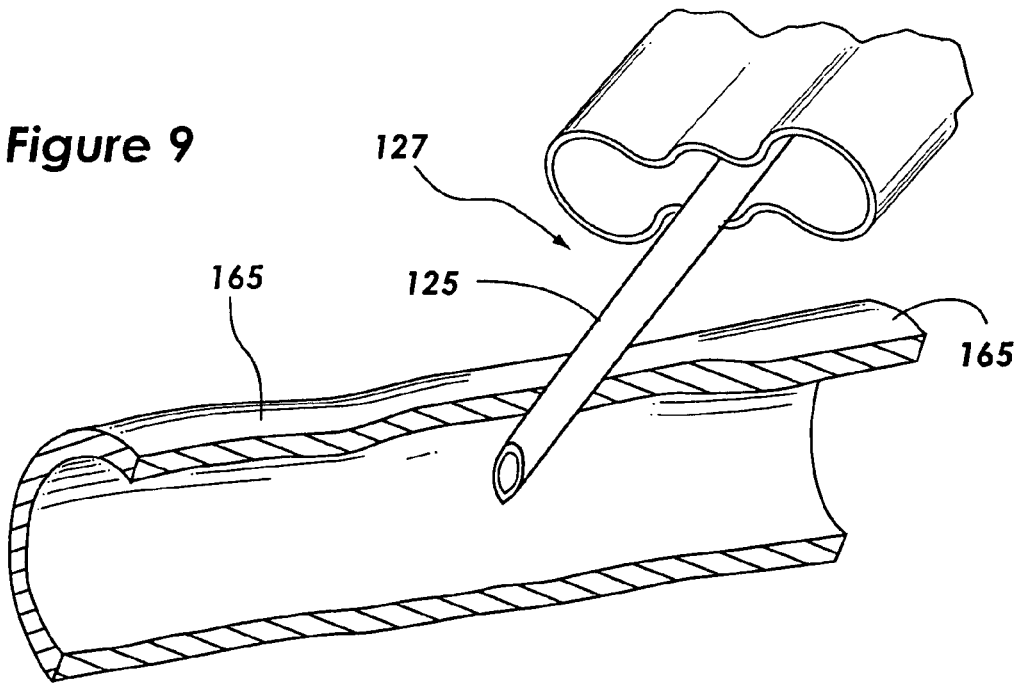
FIG. 9 is a perspective view of the vascular closure system of FIG. 1 illustrating the access needle extending from the center lobe of the sheath and into the vessel.
Figure 10:
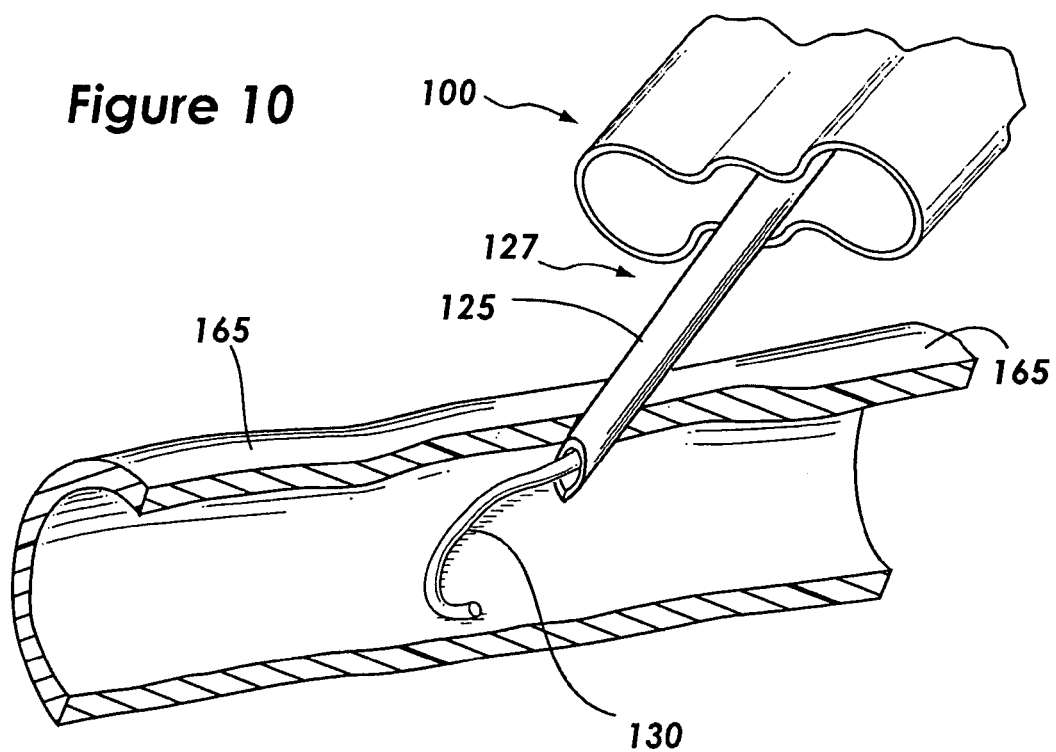
FIG. 10 is a perspective view of the vascular closure system of FIG. 1 illustrating the guide wire extending out from the access needle and traveling along the interior wall of the vessel.
Figure 11:
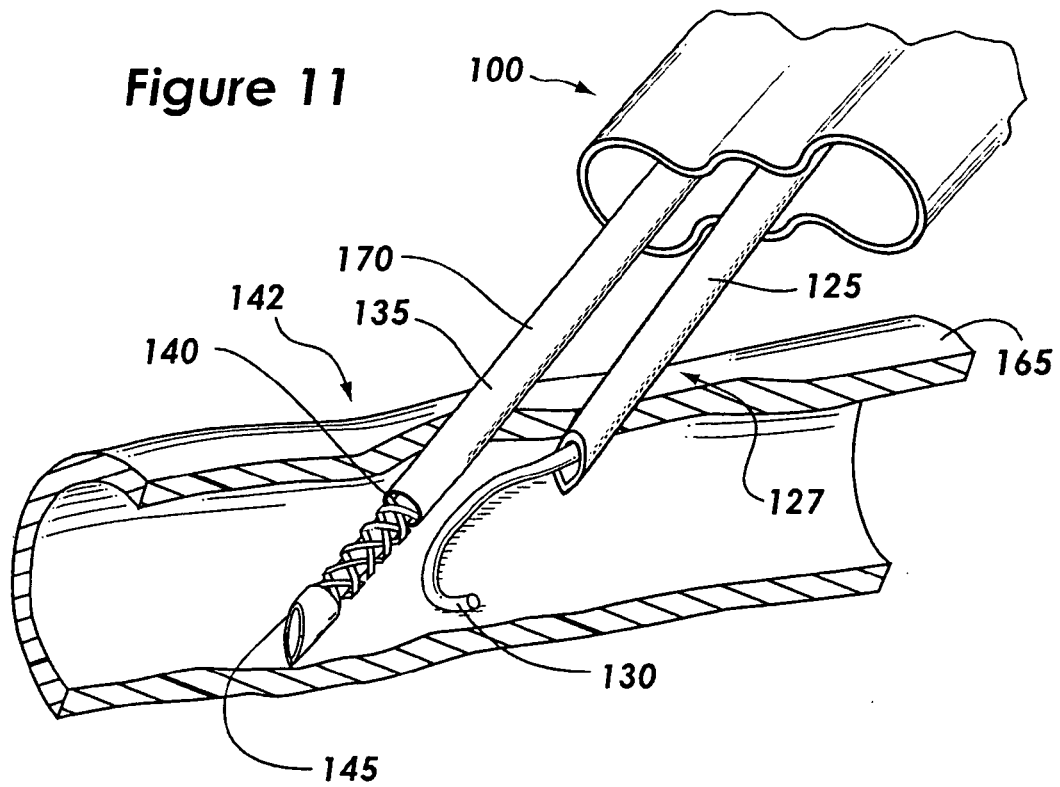
FIG. 11 is a perspective view of the vascular closure system of FIG. 1 illustrating the expandable needle extending from left lobe of the sheath and into the vessel.
Figure 12:
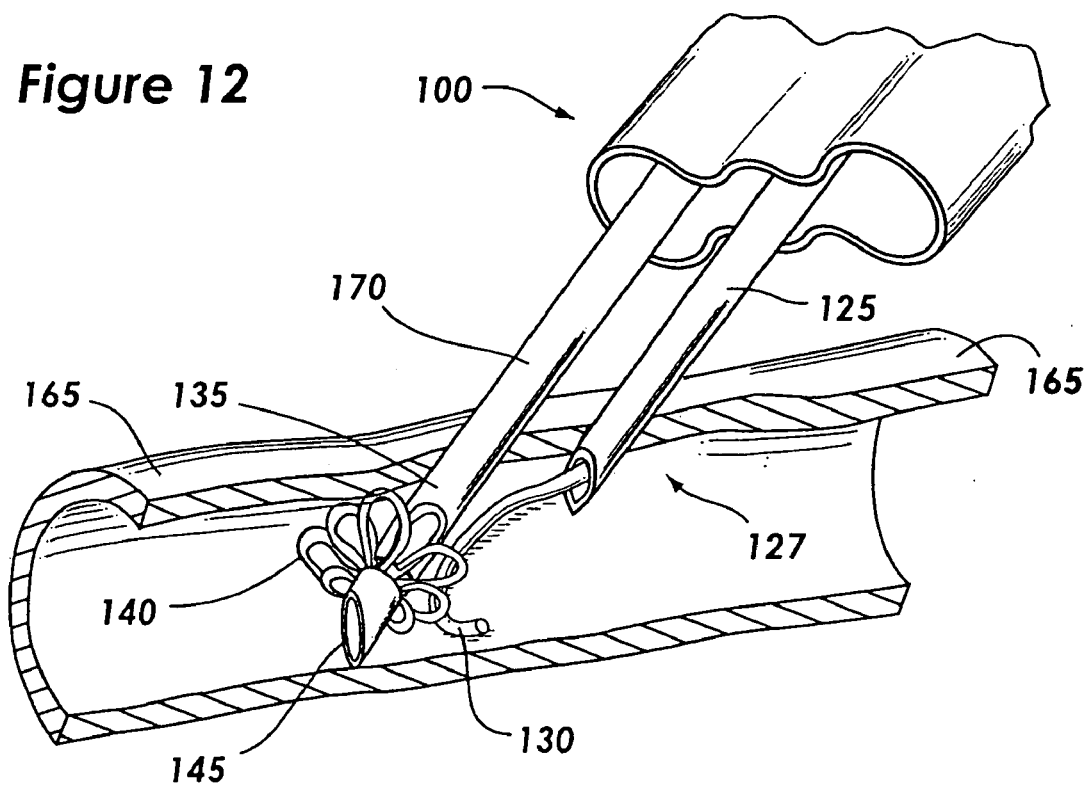
FIG. 12 is a perspective view of the vascular closure system of FIG. 1 illustrating the expandable needle being retracted into an expanded state.
Figure 13:
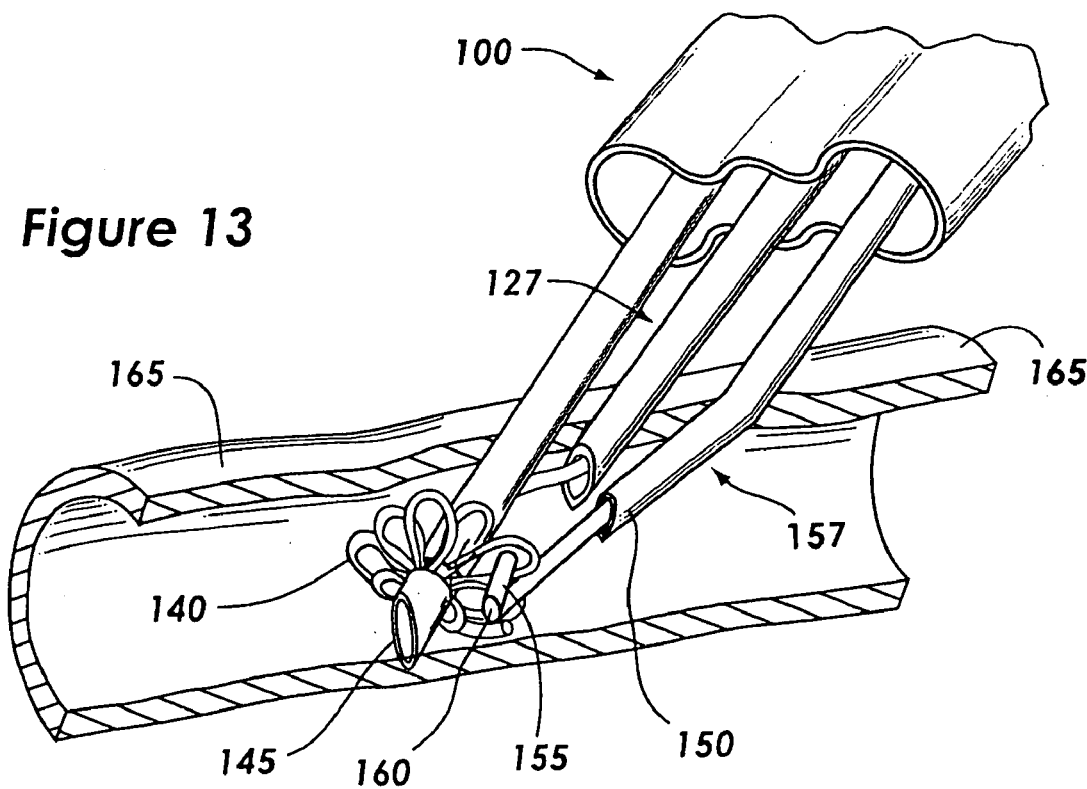
FIG. 13 is a perspective view of the vascular closure system of FIG. 1 illustrating the hooking device being extended into the vessel from the right lobe of the sheath, wherein the piercing toggle is hooked into one of the loops of the expanded needle.
Figure 14:
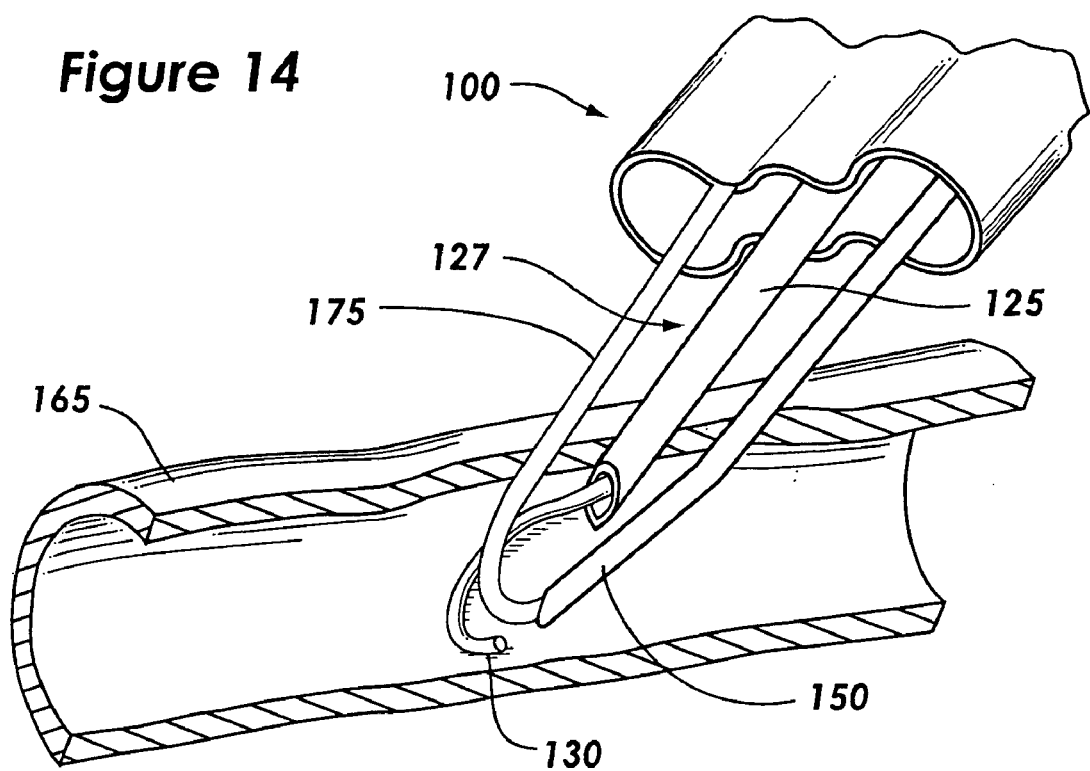
FIG. 14 is a perspective view of the vascular closure system of FIG. 1 illustrating a suture being extended from the left lobe of the sheath and down into the vessel via a curved needle after the expandable needle was retracted back into the left lobe of the sheath.
Figure 15:
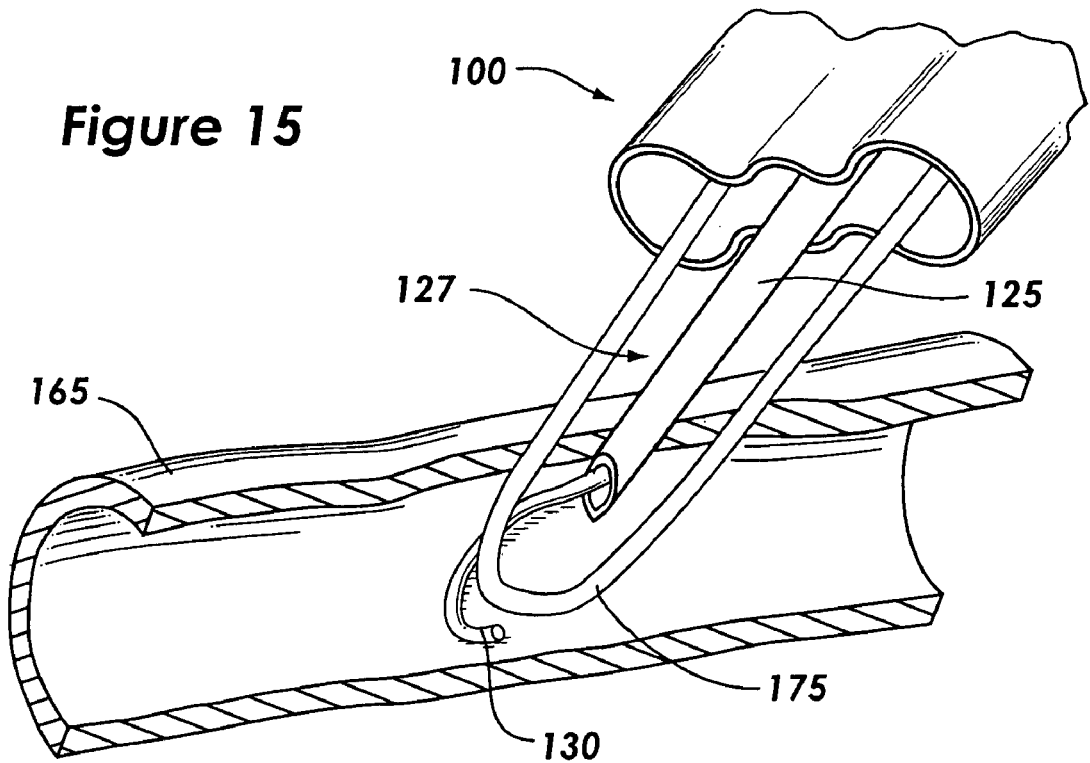
FIG. 15 is a perspective view of the vascular closure system of FIG. 1 illustrating a suture extending from the left lobe of the sheath down through the vessel and back up to the right lobe of the sheath after the curved needle was retracted into the right lobe of the sheath, wherein the guide wire is still positioned within the vessel.
Figure 16:
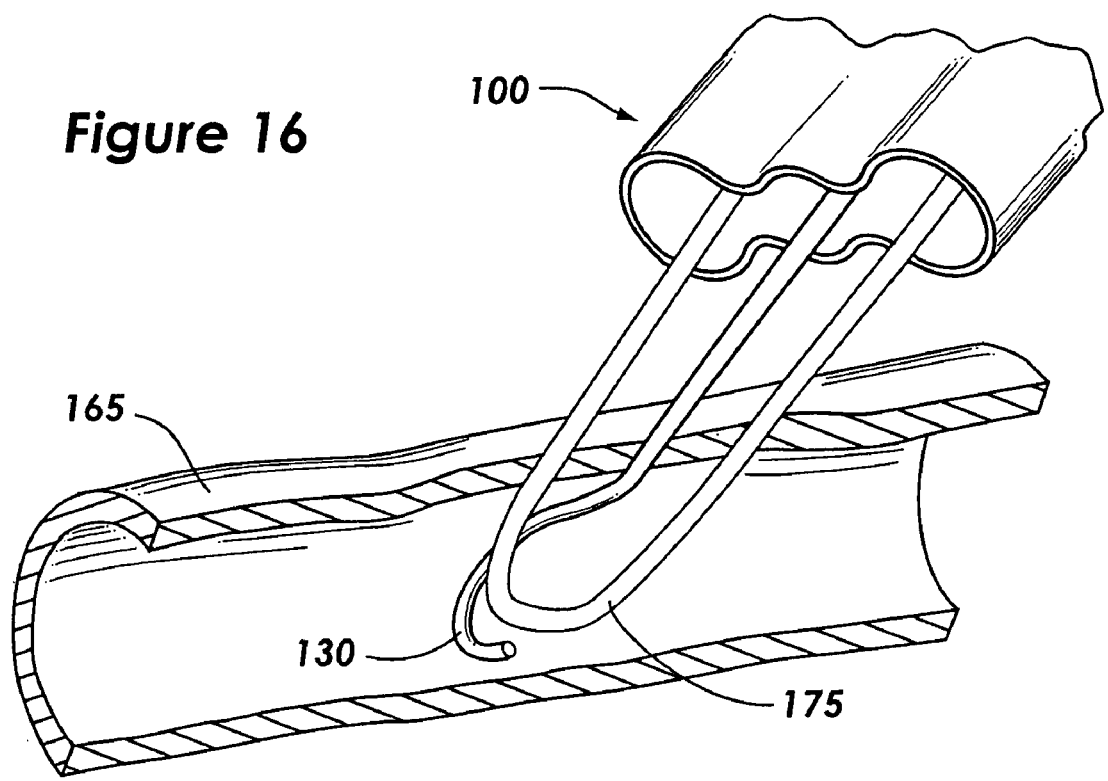
FIG. 16 is a perspective view of the vascular closure system of FIG. 1 illustrating a suture extending from the left lobe of the sheath down through the vessel and back up to the right lobe of the sheath.
Figure 17:
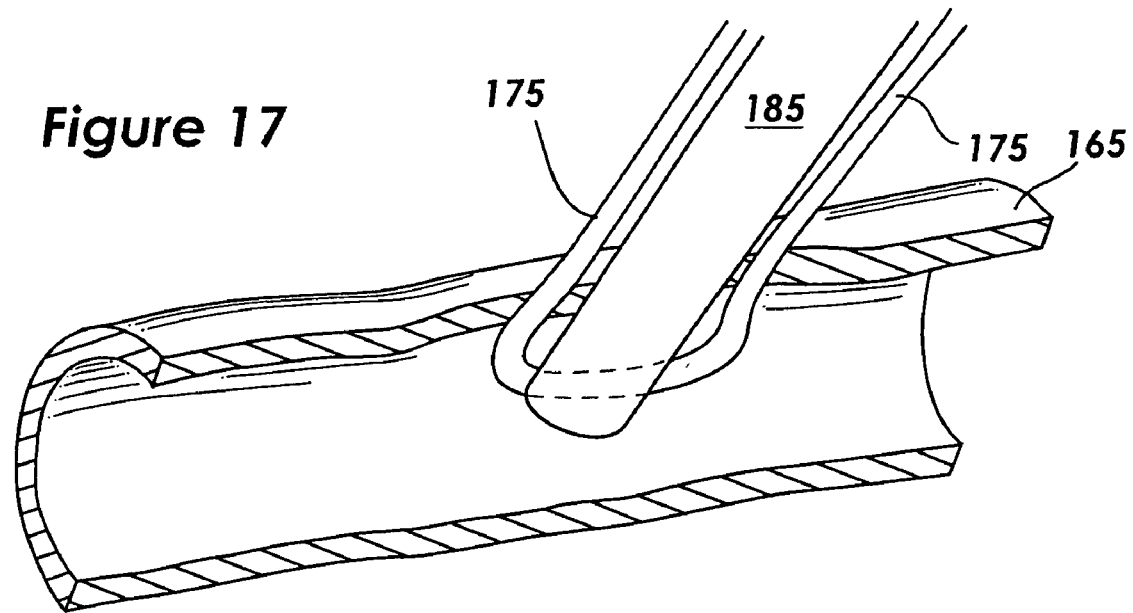
FIG. 17 is a perspective view of an introducer sheath arteriotomy with the suture pushed out of the way.

FIGS. 8–17 illustrate the process by which one embodiment of the vascular closure system of the present invention closes an opening in a vessel. Initially, the vascular closure device is positioned above the vessel 165 as shown in FIG. 8. The guiding device 127 is then extended from the center lobe 110 of the sheath 100 as shown in FIG. 9. The access needle 125 pierces the vessel 165 or is inserted into an existing opening in the vessel. The guide wire 130 is extended from the access needle 125 and conforms to a portion of the interior surface of the vessel 165 as shown in FIG. 10. The guiding device 127 thereby provides tactile feedback as to the proper location of the vascular closure device in relation to the vessel 165. The expandable needle 142 is then extended into the vessel 165 via a different opening as shown in FIG. 11. The expandable needle 142 utilizes the needle tip 145 to pierce the vessel 165 in order to create the additional opening into the vessel. The expandable mesh 140 is then expanded by extending the actuator 135 distally creating a compression force between the actuator 135 and the needle tip 145, as shown in FIG. 12. Alternatively, the mesh 140 can be expanded by retracting the entire expandable needle tip 145 while maintaining compressive force on the actuator rod 135. The hooking device 157 is then extended into the vessel 165 through yet another opening as shown in FIG. 13. The tip 160 of the curved needle 150 pierces the vessel 165 to allow the hooking device 157 to access the vessel 165 as shown. The piercing toggle 155 automatically hooks into the expandable mesh 140 of the expandable needle 142. Alternatively, additional steps may be performed in order to ensure that the hooking device 157 properly hooks into the expandable needle 142. The expandable needle 142 is retracted back up into the sheath 100 thereby extending the suture 175 out from the curved needle 150 as shown in FIG. 14. The hooking device 157 is also retracted back into the sheath 100 creating an internal suture pass through the vessel 165 as shown in FIG. 15. As shown in FIG. 16, the guiding device 127 is retracted back into the sheath 100 leaving the internal suture pass and the guide wire. As shown in FIG. 17, a procedure sheath 185 is subsequently inserted into the vessel opening and the suture 175 is pushed to one side or out of the way of the sheath 185. One of any number of medical procedures can thus be performed via sheath 185.

After a medical procedure has been performed via sheath 185, various techniques for approximating an opening can then be used to approximate tissue surrounding the vessel opening. For example, the two ends of the suture 175 could be joined to form a suitable knot that may be slidable down over an opening to create a sealing pressure on the opening. Alternatively, other vessel opening procedures can be utilized. In this manner the opening can efficiently be sealed thereby promoting rapid homeostasis.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure system, comprising:
  a sheath including a plurality of hollow lobes;
  a guiding device disposed within one of the hollow lobes;
  an expandable needle disposed within a different one of the hollow lobes; and
  a hooking device disposed within yet another different one of the hollow lobes, wherein the hooking device is configured to hook the expandable needle.

2. The vascular closure system of claim 1 wherein the sheath includes three hollow cylindrical lobes.

3. The vascular closure system of claim 1 wherein the sheath comprises a distal profile capable of dilating tissue.

4. The vascular closure system of claim 1 wherein the guiding device further comprises:
  an access needle; and
  a guide wire configured to conform to the shape of the interior surface of a vessel.

5. The vascular closure system of claim 1 wherein the guiding device further comprises:
  an access needle; and
  a bent guide wire configured to conform to the shape of the interior surface of a vessel.

6. The vascular closure system of claim 1 wherein the guiding device comprises an expandable foot.

7. The vascular closure system of claim 1 wherein the guiding device is configured to be inserted into a first opening in a vessel, the expandable needle is configured to be inserted into a second opening in the vessel, and the hooking device is configured to be inserted into a third opening in the vessel.

8. The vascular closure system of claim 1 wherein the sheath includes three lobes, a left lobe, a center lobe and a right lobe, and wherein the guiding device is disposed within the center lobe, the expandable needle is disposed within the left lobe, and the hooking device is disposed within the right lobe.

9. The vascular closure system of claim 1 wherein the expandable needle further comprises:
   a needle tip configured to pierce the surface of a vessel;
   an expandable mesh that includes an expanded state and an extended state;
   an insertion rod configured to insert the expandable needle without expanding the expandable mesh; and
   an actuator configured to expand the expandable mesh into the expanded state.

10. The vascular closure system of claim 1 wherein the hooking device further comprises:
    a curved hollow needle configured to pierce the surface of a vessel;
    a suture extending through the curved hollow needle; and
    a piercing toggle connected to the suture and disposed on an end of the curved hollow needle such that a contiguous piercing surface is formed with the end of the curved hollow needle and the piercing toggle.

11. The vascular closure system of claim 1 wherein the hooking device further comprises:
    a tubular curved hollow needle configured to pierce the surface of a vessel;
    a degradable suture extending through the curved hollow needle; and
    a piercing toggle connected to the suture and disposed on an end of the curved hollow needle such that a contiguous piercing surface is formed with the end of the curved hollow needle and the piercing toggle, wherein the piercing toggle is shaped to provide an efficient hooking surface.

12. A vascular closure system, comprising:
    a sheath including three hollow lobes;
    a guiding device disposed within one of the hollow lobes, wherein the guiding device further includes:
      an access needle;
      a guide wire configured to conform to the shape of the interior surface of a vessel;
    an expandable needle disposed within a different one of the hollow lobes, wherein the expandable needle further includes:
      a needle tip configured to pierce the surface of a vessel;
      an expandable mesh that includes an expanded state and an extended state;
      an insertion rod configured to insert the expandable needle without expanding the expandable mesh;
      an actuator configured to expand the expandable mesh into the expanded state;
    a hooking device disposed within yet another different one of the hollow lobes, wherein the hooking device is configured to hook the expandable needle, wherein the hooking device further includes:
      a curved hollow needle configured to pierce the surface of a vessel;
      a suture extending through the curved hollow needle; and
      a suture extending through the curved hollow needle and a toggle connected to the suture and disposed on the end of the curved hollow needle.

* * * * *